(12) United States Patent
Pelletier (10) Patent No.: US 7,581,435 B2
(45) Date of Patent: Sep. 1, 2009

(54) METHOD AND APPARATUS FOR ACQUIRING PHYSICAL PROPERTIES OF FLUID SAMPLES AT HIGH TEMPERATURES AND PRESSURES

(75) Inventor: Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 382 days.

(21) Appl. No.: 11/240,832

(22) Filed: Sep. 30, 2005

(65) Prior Publication Data
US 2006/0070426 A1    Apr. 6, 2006

Related U.S. Application Data

(60) Provisional application No. 60/615,561, filed on Oct. 1, 2004.

(51) Int. Cl.
*G01N 11/04* (2006.01)
(52) U.S. Cl. .................................. 73/54.02; 73/54.07
(58) Field of Classification Search ............... 73/54.02, 73/54.04–54.09
See application file for complete search history.

(56) References Cited

U.S. PATENT DOCUMENTS

| 4,425,810 | A | 1/1984 | Simon et al. |
| 4,543,819 | A | 10/1985 | Chin |
| 5,747,674 | A | 5/1998 | Moracchini et al. |
| 5,756,884 | A | 5/1998 | Moracchini et al. |
| 6,578,409 | B1 | 6/2003 | Zhou et al. |

FOREIGN PATENT DOCUMENTS

| DE | 3210012 A1 | * | 9/1983 | ................ 73/54.04 |
| EP | 0 473 472 | | 3/1992 | |
| GB | 2 188 437 | | 9/1987 | |
| GB | 2233461 A | * | 1/1991 | ................ 73/54.09 |
| JP | 02210244 A | * | 8/1990 | ................ 73/54.06 |
| JP | 03002645 A | * | 1/1991 | ................ 73/54.05 |
| JP | 03082952 A | * | 4/1991 | ................ 73/54.02 |

OTHER PUBLICATIONS

EPO abstract of EP 473472 A1, Behar et al., Mar. 1992.*
Derwent abstract of patent family of EP 473472 A1, Behar et al., Mar. 1992, Derwent-ACC-No: 1992-073937.*
Ungerer, C. et al., "Measurement and Prediction of Volumetric and Transport Properties of Reservoir Fluids at High Pressure", Revue de L'Institut Francas du Petrole, vol. 53, No. 3, May-Jun. 1998, pp. 265-281.
Akkarachittoor, Narayanan S., "Dual chamber capillary viscometer for viscosity measurements of concentrated polymer solutions at elevated temperatures", *Review of Scientific Instruments*, 57(6), (Jun. 1986),1182-1184.

* cited by examiner

*Primary Examiner*—Thomas P Noland
(74) *Attorney, Agent, or Firm*—Schwegman, Lundberg & Woessner, P.A.

(57) ABSTRACT

Embodiments of the present invention are directed to an apparatus for acquiring physical properties of a fluid sample at high temperatures and pressures. The apparatus comprises a sample manifold, one or more pressure intensifiers to push or pull a sample through the sample manifold, and a viscosity coil to receive a part of the sample to measure a viscosity of the sample.

15 Claims, 8 Drawing Sheets

METHOD AND APPARATUS FOR ACQUIRING PHYSICAL PROPERTIES OF FLUID SAMPLES AT HIGH TEMPERATURES AND PRESSURES

PRIORITY OF INVENTION

This non-provisional application claims the benefit of priority under 35 U.S.C. § 119(e) to U.S. Provisional Patent Application Ser. No. 60/615,561, filed Oct. 1, 2004, which is herein incorporated by reference.

TECHNICAL FIELD

The application relates generally to fluid analysis. In particular, the application relates to an oil reservoir fluid analysis at high temperatures and pressures done in the field, in a hazardous environment and that benefits from adherence to explosion proof equipment design and standards.

BACKGROUND

In the search for hydrocarbons, the determination of the physical properties of the reservoir fluids is required to make the decisions concerning the economic value and reservoir management. Traditionally, samples have been taken in the field at either bottom hole, the separator or at the stock tank. These samples were then shipped to a laboratory where the fluid was reconstituted to reservoir conditions and then a number of properties measured. The properties of greatest interest immediately after a sample is taken are saturation pressure, viscosity, relative volume, compressibility at reservoir temperature and finally, composition of the sample.

Currently, the quality of the results is a measure of the care, dedication and attention to minute detail of expensive laboratory staff. The test results are subject to the limits imposed by staff endurance and attention span. Some samples require extremes in pressure, temperature and quite often, both at the same time. In addition, some samples contain materials which are toxic, such as hydrogen sulfide. Toxic samples typically require measurement procedures which are time consuming, cumbersome and often degrade the measurement quality of the sample. The time between the acquisition of a sample and the completion of a laboratory program has traditionally varied from weeks to nearly a year. The current petroleum exploration and operation environments require a subset of the physical property data at increasingly earlier time frames. Field locations are accommodation and space limited. While small laboratories can and have been placed on drilling rigs, proper staffing, safety and bed space has always been contentious.

BRIEF DESCRIPTION OF THE DRAWINGS

Embodiments of the invention may be best understood by referring to the following description and accompanying drawings which illustrate such embodiments. In the drawings.

DETAILED DESCRIPTION OF THE EMBODIMENTS OF THE PRESENT INVENTION

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The embodiments of the present invention relate acquiring the physical properties of a sample at high temperature and pressure.

Definitions

In some embodiments, "sample" refers to a representative portion of a whole. Further, sample may be defined as a small segment or quantity taken as evidence of the quality or character of the entire group or lot. Gove, Philip Babcock, ed. *Webster's Third New International Dictionary*, Springfield, Mass., 1993 p. 2008. An example of a sample may be drilling fluid, reservoir fluid or downhole gases. Samples may be in gas, solid or liquid form.

In some embodiments, "sample manifold" refers to the component of an apparatus in which a sample is passed. The sample manifold of the present invention may include inlet valves, viscosity coils, bypass valves and sensors to manipulate and measure the properties of a sample.

In some embodiments, "pressure intensifier" refers to a chamber consisting of a piston or pistons which act to put pressure on or remove pressure from a sample. A pressure intensifier may contain a sample piston, hydraulic support piston and a piston position measurement device to measure the movement of the one or more pistons. The pressure intensifier may also contain drive fluid, hydraulic support fluid and sample.

In some embodiments, "viscosity" refers to the physical property of a fluid or semifluid that enables it to develop and maintain a certain amount of shearing stress dependent upon the velocity of flow and then to offer continued resistance to flow. Gove, Philip Babcock, ed. *Webster's Third New International Dictionary*, Springfield, Mass., 1993 p. 2557.

In some embodiments, "viscosity coil" refers to a capillary tube with known dimensions used to measure the viscosity of a sample.

In some embodiments, "hydraulic support piston" refers to a piston in contact with hydraulic support fluid. The hydraulic support piston usually has a larger surface area than the sample piston in order to intensify the pressure on the sample with small movements of the hydraulic support piston.

In some embodiments, "sample piston" refers to a piston in contact with a sample and drive fluid. The sample piston usually has a smaller surface area than the hydraulic support piston in order to amplify the pressure changes on a sample with small movements of the hydraulic support piston.

In some embodiments, "hydraulic support fluid" refers to a fluid in contact with the hydraulic support piston and used in the movement of the piston. The hydraulic support fluid may be water or a hydraulic fluid, for example.

In some embodiments, "drive fluid" refers to a fluid in contact with the sample piston and used in the movement of the piston. The drive fluid may be water or a hydraulic fluid, for example.

In some embodiments, "viscosity bypass" refers to a valve or line used to move a sample around a viscosity coil.

In some embodiments, "drive mechanism" refers to the pneumatically powered system of drive fluid used to push or pull the pistons in a pressure intensifier. The drive mechanism may utilize a gas, such as nitrogen or compressed air.

In some embodiments, "optical cell" refers to device used to view or monitor a sample in-line. The optical cell may contain a viewing window and light source. The light source may be visible light, infrared or X-ray, for example. Analytical instruments, such as spectrometers, may be coupled to an optical cell for analysis.

In some embodiments, "hydraulic support fluid reservoir" refers to a tank or containment device used to store hydraulic support fluid. The hydraulic support fluid reservoir may accept hydraulic support fluid from the constant volume metering assembly or be used to draw hydraulic support fluid into the apparatus.

In some embodiments, "constant volume metering assembly" refers to the device used to draw a measured amount of hydraulic support fluid into or out of the apparatus. The constant volume metering assembly consists of an inlet valve and outlet valve with actuators and is activated pneumatically. Between the inlet and outlet valves lies the constant volume discharge cylinder in which a measured amount of hydraulic support fluid is collected. The cylinder contains a piston to discharge the fluid and may be spring loaded or activated pneumatically.

In some embodiments, "hydraulic fluid" refers to a fluid usually of low viscosity used in a hydraulically operated mechanism. Gove, Philip Babcock, ed. *Webster's Third New International Dictionary*, Springfield, Mass., 1993 p. 1107. Hydraulic fluid may be used as the hydraulic support fluid or drive fluid in embodiments of the present invention.

In some embodiments, "piston position measurement device" refers to a device which accurately measures the movement of pistons in a pressure intensifier.

In some embodiments, "spectrometer" refers to an instrument that measures interactions of various types of radiation with matter. A radiation source first interacts with a sample. A detector may then record the type of interaction, such as absorbance, transmittance or emission. The electrical signals from the detector may be converted to useful numbers or a visual display such as a spectrum. Skoog, Douglas A., et. al., *Principles of Instrumental Analysis*, 5th Ed., Philadelphia 1998, p. 116. Examples of types of spectrometers used may include Fourier Transform Infrared Spectrometers (FTIR) and Tunable Diode Laser Spectrometers (TDLS).

In some embodiments, "homogeneous" refers to a uniform structure or composition throughout. Gove, Philip Babcock, ed. *Webster's Third New International Dictionary*, Springfield, Mass., 1993 p. 1084. A sample may be homogeneous or substantially homogeneous after mixing, for example.

In some embodiments, "compositional analysis" refers to analyzing the composition of a sample. The compositional analysis may be accomplished by using such methods as gas chromatography, high performance liquid chromatography, laser spectroscopy or mass spectrometry, for example.

In some embodiments, "bubble point" refers to the point in the expansion of a liquid in which the pressure drops enough to allow the escape of the first molecules in gaseous form. McCain, William D., *The Properties of Petroleum Fluids*, 2nd Ed., Tulsa, Okla. 1990, p. 62.

In some embodiments, "volumetric" refers to or relates to the measurement of volume. Gove, Philip Babcock, ed. *Webster's Third New International Dictionary*, Springfield, Mass., 1993 p. 2563. Examples of volumetric properties may include total system volume, volume measurements of different phases of a sample, relative volumes and compressibility. The volumetric properties of a substance are measured most commonly at constant pressure and temperature is varied.

In some embodiments, "total sample volume" refers to the volume of a sample within an apparatus. The total sample volume may be measured once the sample has been loaded into the apparatus. During the process of expanding the sample, the pressure will concomitantly fall. At some point a liquid sample may evolve a gas, and a gas may condense out of a liquid. The resulting gas volume in combination with the liquid volume make up the total sample volume.

In some embodiments, "compressibility" refers to the capability of compression. Gove, Philip Babcock, ed. *Webster's Third New International Dictionary*, Springfield, Mass., 1993 p. 467. Compressibility is further described as a fluid property. McCain, William D., *The Properties of Petroleum Fluids*, 2nd Ed., Tulsa, Okla. 1990, pp. 231-236. Compressibility may be calculated according to the following formula:

$$C = -1/V(\delta V/\delta P)_T; \text{ where}$$

C is the isothermal compressibility; V is the total system volume; $\delta V$ is the partial derivative of volume; P is the pressure; $\delta P$ is the partial derivative of pressure and T indicates the temperature is held constant. The equation above gives the fractional change in volume of a liquid as pressure is changed at constant temperature. Compressibility of a fluid may be measured by the embodiments of the present invention.

In some embodiments, "differential pressure" refers to the difference between two pressures. A differential pressure may be measured across a viscosity coil or sample line.

In some embodiments, "flow rate" refers to a measurement of the amount of a liquid or gas which passes a fixed point in a given time.

In some embodiments, "total system volume" refers to the volume of sample at the current pressure. The temperature is assumed to be fixed.

In some embodiments, "relative volumes" are ratios of the specified phase divided by a reference volume, such as the bubble point volume of the sample. At pressures below the bubble point, relative volume must be specified according to the phases of the sample, liquid or gas.

In some embodiments, "infrared energy" refers to radiation in the electromagnetic spectrum with wavenumbers ranging from about 12,800 to about 10 cm$^{-1}$ or wavelengths from about 0.78 to about 1000 μm. Further, in some embodiments, mid-infrared energy refers to the range of about 2.5 to about 50 µm or about 4000 to about 200 cm$^{-1}$. Further, in some embodiments, near-infrared energy refers to the range of about 0.78 to about 2.5 µm or about 12,800 to about 4000 cm$^{-1}$. Skoog, Douglas A., et. al., *Principles of Instrumental Analysis*, 5$^{th}$ Ed., Philadelphia 1998, p. 380-381.

In some embodiments, "UV-Vis" or "ultra violet-visible" refers to radiation in the electromagnetic spectrum with wavelengths from about 100 to about 780 nm. Skoog, Douglas A., et. al., *Principles of Instrumental Analysis*, 5$^{th}$ Ed., Philadelphia 1998, p. 300.

In some embodiments, "X-ray fluorescence" refers to the bombardment of a sample for chemical analysis with X-rays. The light which the sample emits may indicate which chemicals are present and the relative proportions in which they occur. X-ray fluorescence may be used in connection with an optical cell for analysis.

Figure 1:
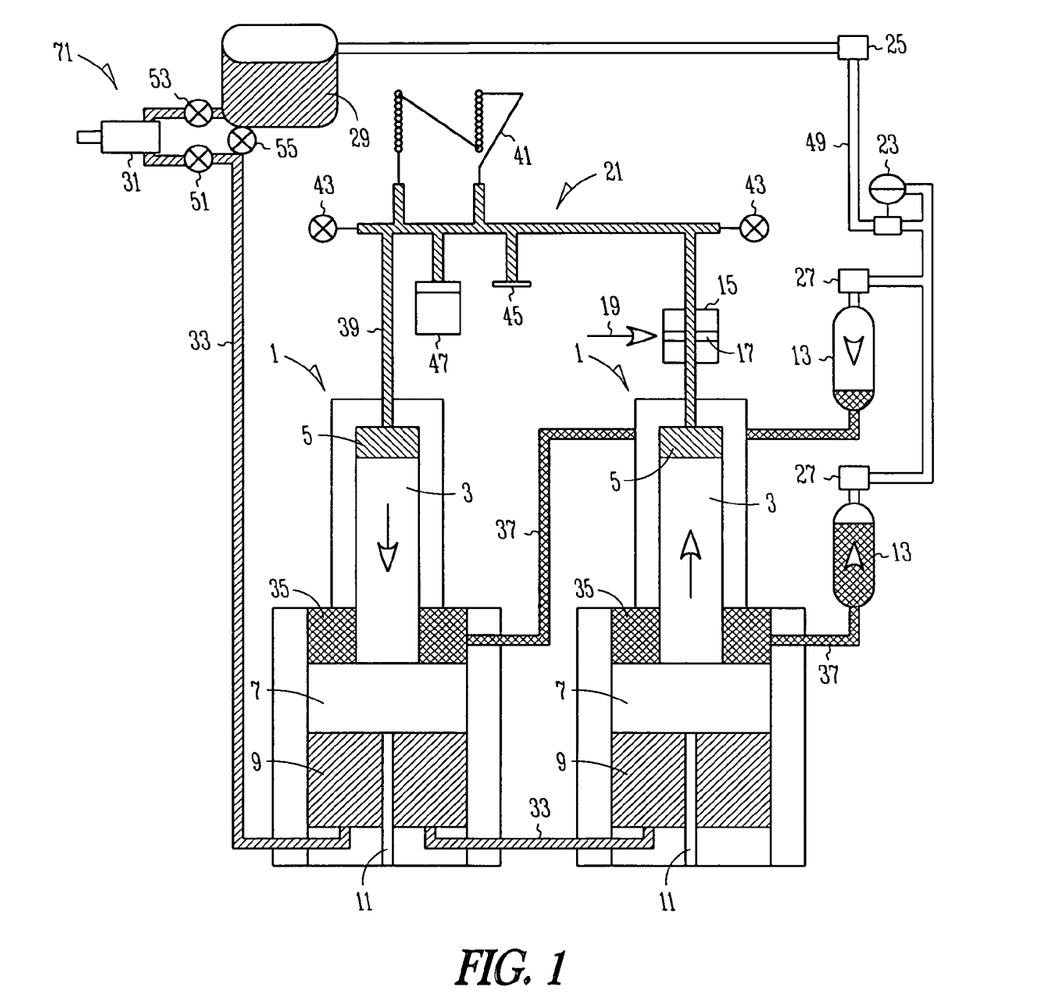
FIG. 1 illustrates an apparatus for acquiring physical properties of a sample, according to some embodiments of the invention.

Referring to FIG. 1, an apparatus to acquire physical properties of a sample is shown, according to some embodiments of the invention. One or more pressure intensifiers (1) are shown in which a sample piston (3) coupled to a hydraulic support piston (7) operate. Drive fluid (35) and hydraulic support fluid (9) are shown on opposite sides of the hydraulic support piston (7). A piston position measurement device (11) is located in the pressure intensifier (1) to measure the position change of the hydraulic support (7) or sample piston (3). The sample piston (3) is in contact with a sample (5). The sample fluid line (39) contains the sample (5) as it moves from the pressure intensifier (1) through the sample manifold (21). The sample manifold (21) consists of pressure gauges (43), a sample inlet valve (45), a viscosity coil bypass valve (47) and a viscosity coil (41). An optional optical cell (15) is positioned in the sample fluid line (39). The optical cell (15) contains a viewing window (17) and works in conjunction with a light source (19) for viewing or measuring. The hydraulic support fluid line (33) carries the hydraulic support fluid (9) between pressure intensifiers (1) and the hydraulic support fluid reservoir (29). A constant volume discharge cylinder (31) is positioned between the hydraulic support fluid reservoir (29) and the pressure intensifiers (1), which makes up the constant volume metering assembly (71). A constant volume assembly inlet valve with actuator (51), constant volume assembly outlet valve with actuator (53) and fast fill/drain valve (55) are positioned in the hydraulic support fluid line (33). A pneumatic source valve (25) is located in the pneumatic source line (49) which carries a gas to the drive fluid reservoirs (13). A pneumatic valve (27) is positioned adjacent to the drive fluid reservoirs (13). A pressure regulator (23) is positioned in the pneumatic source line (49). A drive fluid (35) is carried by the drive fluid line (37) between the pressure intensifiers (1) and the drive fluid reservoirs (13).

Figure 2:
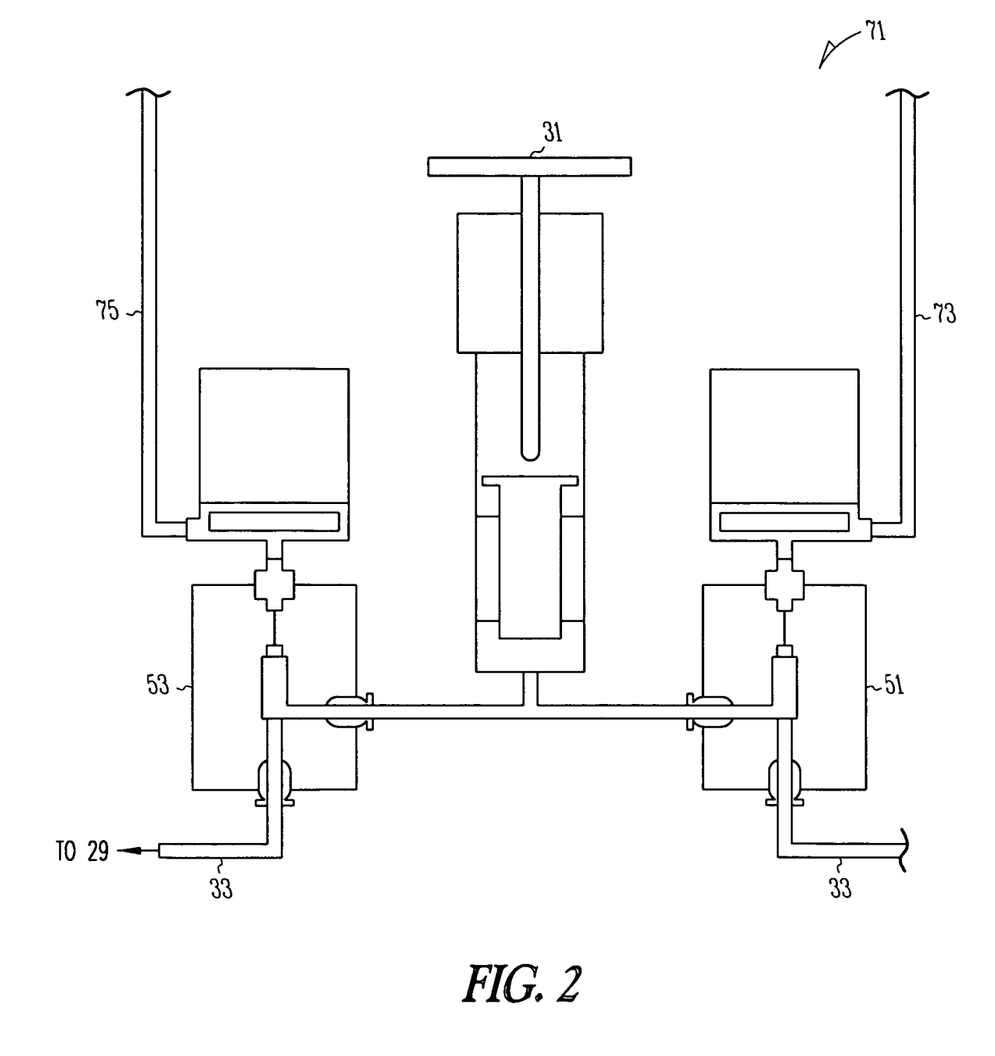
FIG. 2 illustrates a constant volume metering assembly used in an apparatus for acquiring physical properties of a sample, according to some embodiments of the invention.

Referring to FIG. 2, a constant volume metering assembly is shown, used in an apparatus to acquire physical properties of a sample, according to some embodiments of the invention. A constant volume metering assembly (71) contains a constant volume discharge cylinder (31) positioned between a constant volume assembly inlet valve with actuator (51) and a constant volume assembly outlet valve with actuator (53). Pneumatic control line for the inlet valve (73) and pneumatic control line for the outlet valve (75) power the operation of the valves and in this example, the discharge of the constant volume metering cylinder (31).

Figure 3:
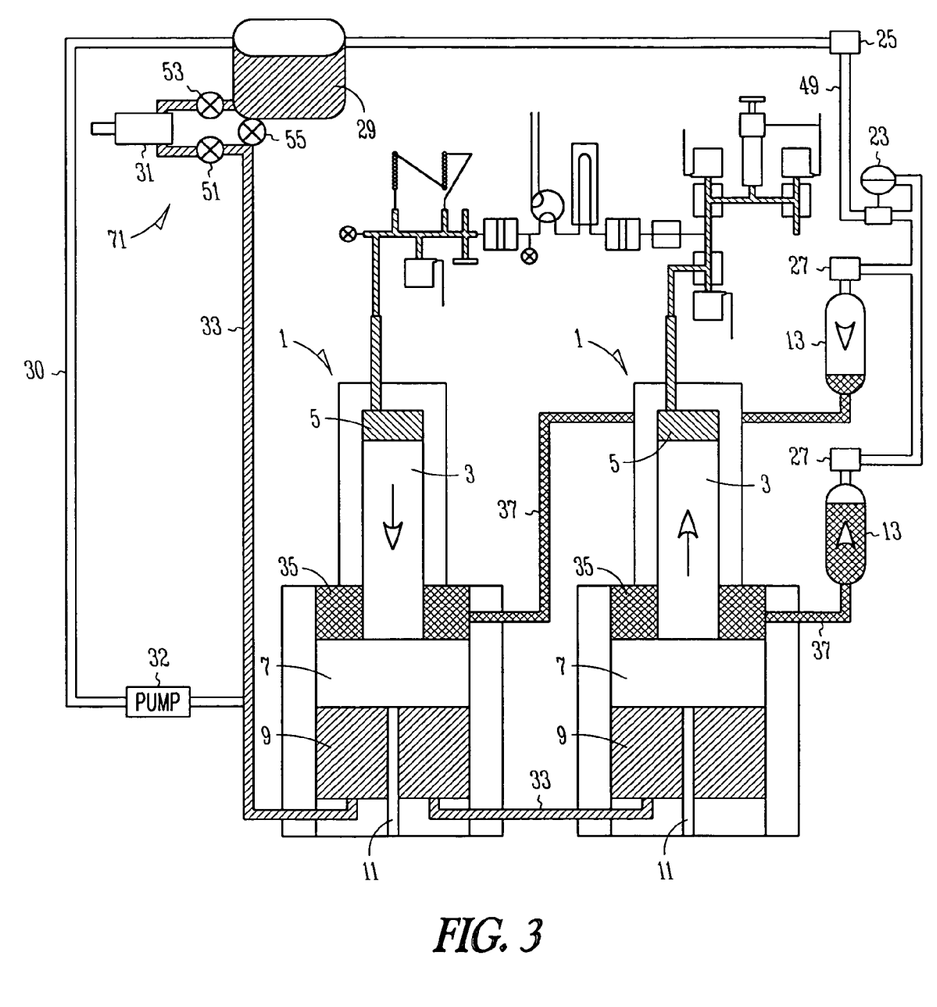
FIG. 3 illustrates an apparatus for acquiring physical properties of a sample, including a re-pressurization feature, according to some embodiments of the invention.

Referring to FIG. 3, an apparatus for acquiring physical properties of a sample, including a re-pressurization feature, is shown, according to some embodiments of the invention. A hydraulic pump (32) is shown connected into the hydraulic support fluid line (33). The hydraulic pump suction line (30) is connected to the hydraulic support fluid reservoir (29). The sample manifold (21) display is cut out and described in FIG. 4.

Figure 4:
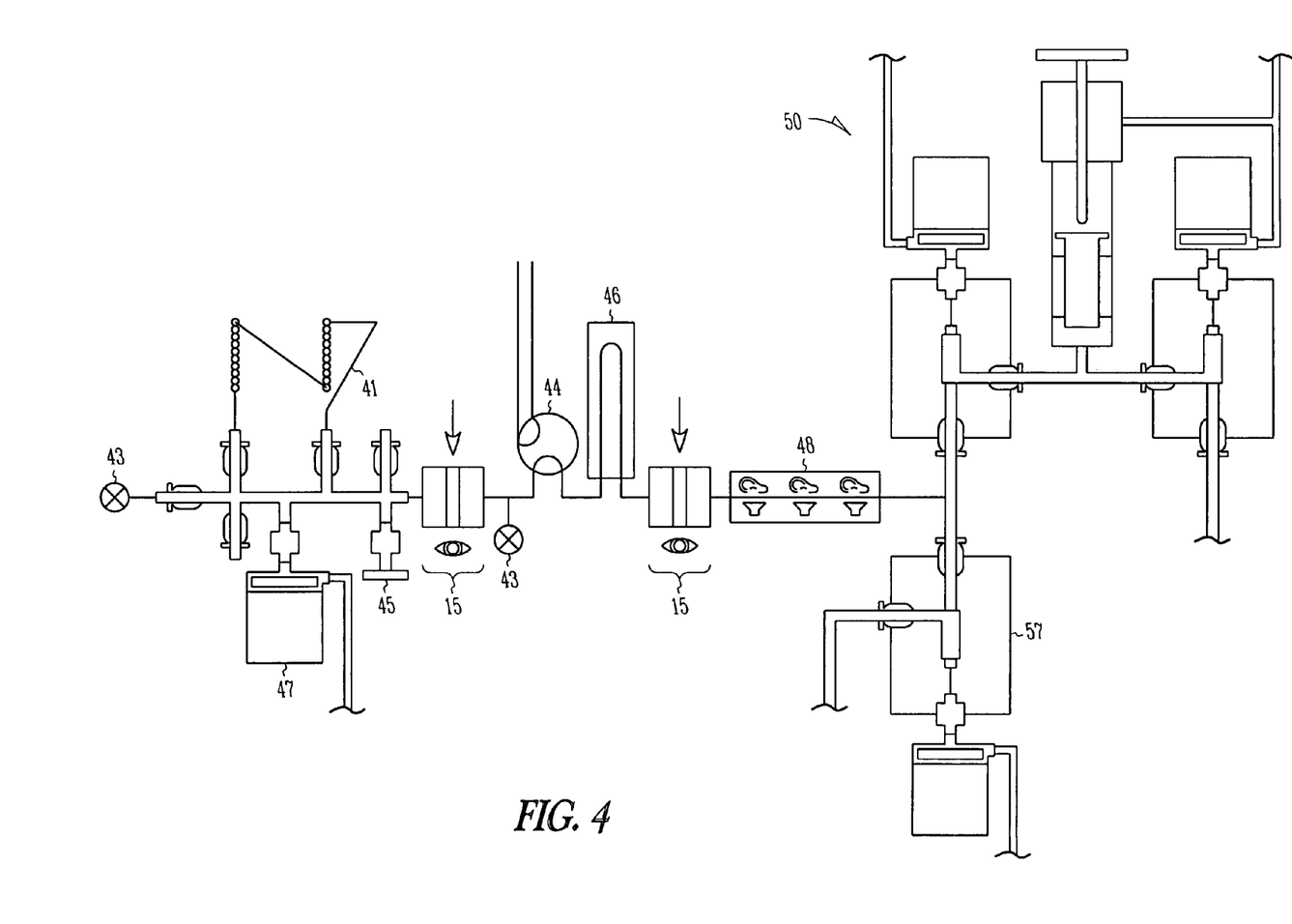
FIG. 4 illustrates a sample manifold used in an apparatus for acquiring physical properties of a sample, according to some embodiments of the invention.

Referring to FIG. 4, a sample manifold is shown, used in an apparatus to acquire physical properties of a sample, according to some embodiments of the invention. A sample manifold (21) contains a viscosity coil (41) with an automated bypass valve (47). Pressure gauges (43) are located on opposite sides of the viscosity coil (41). A sample inlet valve (45) allows for the introduction of a sample (5) into the sample manifold (21). A series of detectors are installed to measure the properties of the fluid (5), this includes optical cells (15), a sampling valve (44), a densitometer (44) and an acoustical properties probe (48). Sample fluids may be metered out of the system by the sample constant volume valve assembly (50). The sample isolation valve (57) connects the sample manifold (21) to the pressure intensifier (1)

Figure 5:
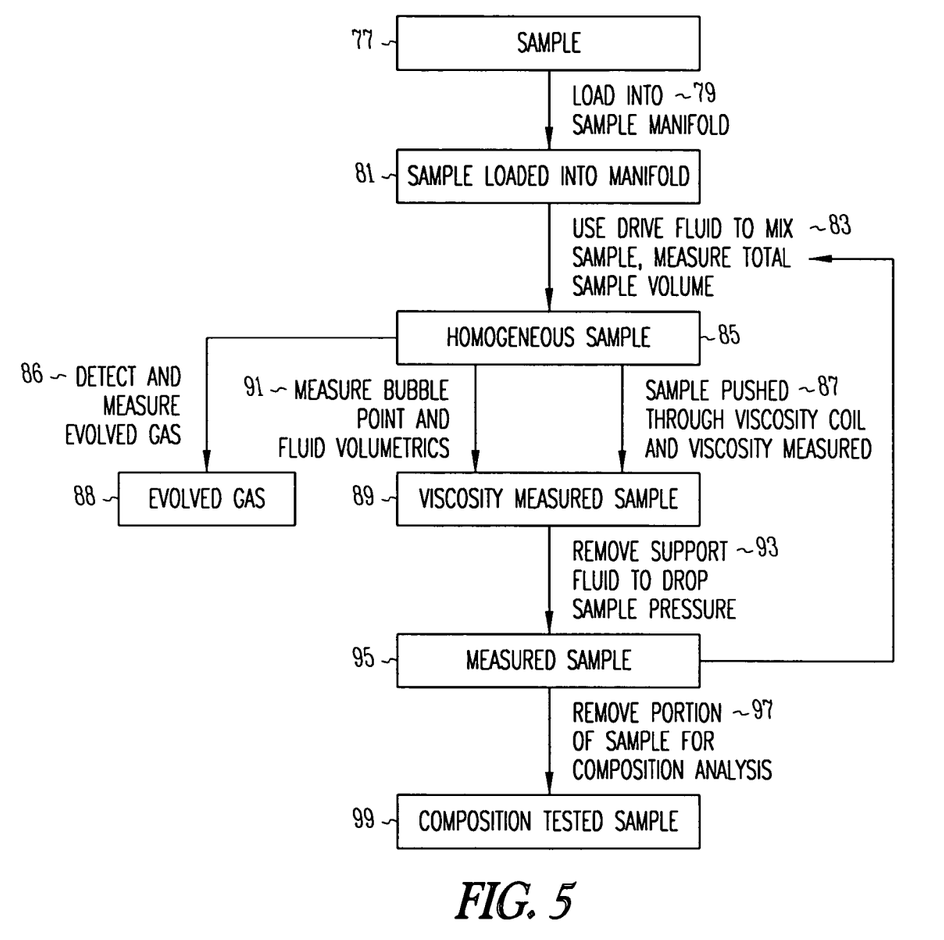
FIG. 5 illustrates a method for acquiring physical properties of a sample, according to some embodiments of the invention.

Referring to FIG. 5, a method to acquire physical properties of a sample is shown, according to some embodiments of the invention. A sample (77) is loaded (79) into a sample manifold (81). Drive fluid is used to force the mixing (83) of the sample (77), producing a homogenous sample (85). The homogeneous sample (85) is pushed through a capillary tube (87) and viscosity and total sample volume is measured (89). The bubble point and fluid volumetrics of the sample are measured (91). Any evolved gas (88) is detected and measured (86). A portion of the measured sample (95) may be removed (97) for compositional analysis (99). Support fluid is removed (93) which drops the sample pressure. The process is repeated (92) by returning to step (83).

Referring to FIGS. 1-4, an apparatus and some components for acquiring physical properties of a fluid are shown. FIG. 1 shows an example of the apparatus system. The entire apparatus may be temperature controlled. A circulated water bath may encompass the apparatus in order to operate under a constant temperature. The apparatus may include one or more pressure intensifiers (1). The pressure intensifier (1) may contain a sample piston (3) in contact with a sample (5). The sample piston (3) may be coupled to a hydraulic support piston (7). The difference in surface areas of the pistons allows for the intensification of pressure due to the law of areas in hydraulics. Minimal movement of the hydraulic support piston (7) with the larger area can produce drastic pressure changes on a sample (5) due to the smaller surface area of the sample piston (3) in contact with the sample (5).

The sample (5) can be made up of a liquid, gas or both. Examples of samples (5) may be reservoir fluid or drilling fluid.

Hydraulic support fluid (9) may be in contact with the hydraulic support piston (7). The hydraulic support fluid (9) may be water or a hydraulic fluid, for example. The hydraulic support fluid (9) exerts or relieves pressure from one side of the hydraulic support piston (7). The drive fluid (35) is in contact with one side of the sample piston (3) and works in the opposite direction of the hydraulic support fluid (9). The drive fluid (35) may be water or a hydraulic fluid. Hydraulic support lines (33) connect the hydraulic support fluid (9) regions of each pressure intensifier (1). Drive fluid lines (37) connect the drive fluid (35) regions of each pressure intensifier (1).

A piston position measurement device (11) is located in one or more pressure intensifiers (1). The piston position measurement device (11) may be any home-made or off-the-shelf device which accurately measures the position changes of at least one of the hydraulic support pistons (7) or sample pistons (3). Changes in the piston positions are used to calculate such properties as viscosity, total sample volume, compressibility and fluid flow rate.

The hydraulic support fluid lines (33) connect the pressure intensifiers to the constant volume metering assembly (71), which controls the release from the system of hydraulic support fluid (7). The constant volume metering assembly (71) (FIG. 2) may consist of a constant volume assembly inlet valve with actuator (51), a constant volume assembly outlet valve with actuator (53), a fast drain/fill valve (55) and a constant volume discharge cylinder (31). The constant volume discharge cylinder (31) contains a piston which discharges the hydraulic support fluid. The piston may be spring loaded or pneumatically activated, for example. The constant volume metering assembly (71) is further connected to the hydraulic support fluid reservoir (29). The hydraulic support fluid reservoir (29) maintains the hydraulic support fluid (9) controlled by the constant volume metering assembly (71). The fast drain/fill valve (55) is optional and allows for the quick draining or filling of hydraulic support fluid (9) into the hydraulic support fluid reservoir (29). In order to manipulate hydraulic support fluid (9) to and from the apparatus, pneumatic control lines for the inlet valve (73) and outlet valve (75) actuate the inlet (51) and outlet (53) valves, which discharges a constant volume into the constant volume discharge cylinder (31). The exact amount introduced or removed can be measured by monitoring the piston position change with the piston position measurement device (11). The addition of the hydraulic pump (32) allows the re-pressurization of the system (FIG. 3). This is necessary if the remainder of a test is to be conducted at a lower temperature, the tests are to be repeated, to compensate for the removal of sample for composition testing or to properly conduct depletion tests. The sample manifold (21) is cut out of FIG. 3 and shown in FIG. 4.

A pneumatic source valve (25) allows for the introduction of a pneumatic source. The pneumatic source for the apparatus may be nitrogen or compressed air. Nitrogen provides the distinct advantage of not supporting combustion as compared to compressed air, which may be more readily available at field locations. The pneumatic source lines (49) connect the pneumatic source to the drive fluid reservoirs (13). A pressure regulator (23) controls the application of the pneumatic source and with limitations, the applied differential pressure to the viscosity coil (41). The drive reservoirs (13) work in opposite directions as they supply drive fluid (35) to the sample piston (3) side of the pressure intensifiers (1). Pneumatic valves (27) are vented at opposite times to push or release drive fluid (35). The pneumatic valves (27) may be automated.

The sample lines (39) contain the flow of sample (5) between pressure intensifiers (1). The sample lines (39) connect with a sample manifold (21), containing valves and coils to manipulate the sample (5). Pressure gauges (43) may be positioned on either side of the sample manifold (21) to measure pressure changes of the sample (5). The sample inlet valve (45) acts as a port to introduce or remove sample (5). The sample (5) is introduced under controlled conditions and during an experimental run, various samples of liquid or gas can be removed for further compositional analysis. A viscosity coil (41) may be made up of capillary tubing of a measured length and diameter. The sample (5) is pushed through the viscosity coil (41) in order to measure the viscosity. The direction of flow is governed by the pneumatic control valves (27). The flow rate of the sample across the viscosity coil (41) can be measured by manipulating time and position measurements from the piston measurement device (11). The sample flow rate can be increased or decreased by changing the set point of the pressure regulator (23). The differential pressure is then monitored between the pressure gauges (43) and flow rate is measured based on the piston movement in order to calculate viscosity based on Poiseuille's Law. The viscosity coil bypass valve (47) may be automated and allows for the sample (5) to flow independent of the viscosity coil (41).

The sample fluid line (39) may contain an optical cell (15). The optical cell (15) has a viewing window (17) to observe the sample and a light source (19). The light source (19) may be as simple as bulb, or as exotic as an electromagnetic radiation source. The detection windows of the optical cell may be fitted with a simple observation lens, other radiation detectors, or an analytical instrument such as a spectrometer or X-ray fluorometer. The illumination and detection axis for the optical cell do not have to be collinear. The types of light may be ultra-violet, visible, infrared or X-ray, for example. The sample fluid lines (39) may also be coupled to additional sensors. Examples of such sensors may be density sensors (46), optical sensors or acoustical probes (48).

A more advanced version of the sample manifold (21) is shown in FIG. 4 and represented as a cut-out of the apparatus in FIG. 3. The sample manifold (21) is shown with a viscosity coil (41), sample inlet valve (45) and pressure gauges (43) similar to that in the more basic version of the sample manifold (21) discussed for FIG. 1. The advanced sample manifold (21) also utilizes a viscosity bypass (47), allowing for the sample to flow around the viscosity coil (41). A cylinder isolation valve (57) allows samples to be segregated where all the sample liquid is below the isolation valve, so that a gas portion of the sample (5) may be removed. The sample constant volume assembly (50) is used to remove sample (5) (gas) in a controlled manner. The sample constant volume assembly (50) operates in a similar manner to the constant volume metering assembly (71) shown previously. Pressure can be maintained by injecting hydraulic support fluid (9) using the hydraulic pump (32). The process of removing a portion or the totality of the gas phase from a sample (5) at regular pressure increments is depletion testing. This models the behavior of the reservoir fluids as they are produced. The procedures are called constant volume depletion and differential liberation testing. The constant volume depletion test is run on a sample which was a gas in the reservoir The differential liberation test is run on a sample which in the reservoir was a liquid. The differential liberation test measures the liquid left in the cell as gas is removed at each incremental extraction. The liquid fractions are measured until atmospheric pressure is reached. The volume of each fraction is divided by the remaining liquid (residual oil) left in the cell when atmospheric pressure and desired temperature (standard temperature) are reached. The resulting value is called the relative oil volume.

The inclusion of the optical cells (15) allows the spectrometric identification of hydrocarbon families and the detection of agglomerated asphaltinic and waxy components in the sample. The acoustical array (48) has been used to detect particulates, both hydrocarbon and inorganic, determine sonic velocities and measure adiabatic compressibility of the sample.

The combination of pneumatic and hydraulic operation of the apparatus allow for use in the field. Coupled with computer control, the apparatus may be nearly autonomous, running experiments unattended for hours and to completion. Unlike larger laboratory measurement devices, embodiments of the current invention do not utilize large mechanical or motor driven pumps. The use of nitrogen in the pneumatics allows for an operational environment free from a risk of combustion. Spark plug and flammability issues need not be addressed by the embodiments of the current invention.

Referring to FIG. 5, a method to acquire physical properties of a sample is shown, according to some embodiments of the invention. Prior to introducing a sample into the apparatus, the sample lines (39) are clean and evacuated. The sample inlet valve (45) is closed. The pistons in the pressure intensifiers (1) are driven to the top of the chambers by manipulating the pneumatic valves (27) on the drive fluid reservoirs (13) and introducing hydraulic support fluid (9) from the hydraulic support fluid reservoir (29). The hydraulic pump (32) may run briefly to increase hydraulic support fluid (9) pressure above the pressure of the sample (5) to be introduced. A sample (77) is then loaded (79) into the sample manifold (81), by opening sample inlet valve (45) and connecting a pressurized container. The sample is introduced slowly, gently and in a manner to preserve sample homogeneity by a person skilled in the arts. The sample is pumped until fluid flow stops. The remaining required volume of sample may be loaded by metering the hydraulic support fluid (9) back into the hydraulic support fluid reservoir (29). This may be accomplished by repeatedly actuating the constant volume metering assembly inlet valve with actuator (51). The piston in the constant volume discharge cylinder (31) moves to the top travel stop. The constant volume assembly inlet valve (51) is then closed. The constant volume assembly outlet valve (53) is then actuated open and the pneumatic source line for the outlet valve (75) delivers pressure to the top of the piston in the constant volume discharge cylinder (31), moving the piston to the bottom travel stop. A metered volume of hydraulic support fluid (9) is delivered back into the hydraulic support fluid reservoir (29). The pneumatic source line for the outlet valve (75) is depressurized and fast drain/fill valve (55) shifts to the closed position. The volume of the fluid sample is then calculated from the piston movements in all pressure intensifiers (1), as measured by the piston position measurement device (11). The sample inlet valve (45) is then shut.

Drive fluid is used to force the mixing (83) of the sample (77), producing a homogenous sample (85). The sample mixing may be specifically accomplished by cycling the actuation of the pneumatic source valves (27), moving the pistons in the pressure intensifiers (1) in opposite directions. One pneumatic source valve (27) delivers pressure while the other vents the source gas to relieve pressure. The pneumatic source line (49) delivers the source gas to the drive mechanism and is maintained by the pressure regulator (23). Pressuring the drive fluid (35) through the drive fluid lines (37) into a pressure intensifier (1), pushes its pistons (hydraulic support piston (7) and sample piston (3)) down, forcing hydraulic support fluid (9) out of the pressure intensifier (1), through the hydraulic support fluid line (33) and into the opposite pressure intensifier (1), pushing its pistons up. This forces the drive fluid (35) from the second pressure intensifier (1) into the drive fluid reservoir (13), in which the source gas is vented through the pneumatic source valve (25). The movement of the sample piston (3) and hydraulic support piston (7) push the sample (5) through the sample manifold (21). The flow of the sample (5) through the sample manifold (21) can be reversed by changing the position of the venting on the pneumatic source valves (27). The mixing can be repeated until the total system volume is stable. The total sample volume can then be measured again of the homogeneous sample.

The homogeneous sample (85) is pushed through a capillary tube (87) and viscosity is measured (89). Viscosity is measured by controlling the differential pressure across the pressure gauges (43) by maintaining the source gas at the pressure regulator (23) and then measuring the flow rate through the viscosity coil (41). The flow rate is measured from the movement of the pistons as recorded by the piston position measurement device (11).

While moving the sample (5) through the viscosity coil (41), the bubble point of the sample (5) may occur which is indicated by a viscosity rate change during measurement. The pressure can then be recorded and the bubble point calculated. If the bubble point has occurred, the gas volume can be measured. The gas volume is measured by moving the pistons in the pressure intensifier (1) to the top of the chamber and switching the pneumatic source valve (27) to move the pistons in the opposite direction. By monitoring the flow rate (piston position movement), a jump in the flow rate can be seen. Measuring the point at which the flow rate jump occurs and the mid-point of the rate increase and rate decrease allows for the calculation of gas phase volume. At this point in the experimental run, the system pressure, total system volume and if present, the gas and liquid volumes can be measured and recorded.

Alternatively, if the advanced manifold is installed, the gas volume can be calculated by noting the indicated volume derived from the piston position measurement device (11). Shifts in transmitted light at one of the optical cells (15) may occur during a complete fluid traverse from one intensifier (1) to the other. The transmitted light changes from low intensity to high in the presence of flowing gas and again back to low when the liquid phase is again being displaced. Similar methodology can be applied to the output signals of the acoustical array (48) and the densitometer (46).

Compressibility of the sample may also be measured based on the movement of the pistons in relation to the incremental pressure change induced by the removal of hydraulic support fluid (93). Compressibility may also be calculated for each phase using the densitometer (46) readings for each phase and the pressure change between each incremental pressure step. The adiabatic compressibility of a phase present in the acoustic array (48) may be independently calculated from the speed of sound in the phase.

Support fluid is removed (93) which drops the sample pressure. Hydraulic support fluid (9) is removed from the apparatus by operating the constant volume metering assembly (71). Specifically, constant volume assembly inlet valve with actuator (51) is opened, which fills the constant volume discharge cylinder (31). The inlet valve (51) is then closed. The constant volume assembly outlet valve (53) is next actuated. The actuation air in pneumatic control line for the outlet valve (75) also drives the piston in the constant volume discharge cylinder (31) to discharge hydraulic support fluid (9) into the hydraulic support fluid reservoir (29). The outlet valve (53) is then closed. The sample is expanded until at least the bubble point is reached (91) and the expansion may be repeated multiple times. Specifically, the expansion may be repeated once a gas phase is present. If the pressure is not at the lower operating limit, the process may begin again at the mixing step.

Optionally, a formation volume factor measurement may be taken. The system temperature is changed to standard temperature and the pressure of the sample is brought to standard pressure. The liquid volume is measured. The reservoir temperature and pressure are then divided by the standard condition liquid volume.

A small portion of the measured sample (95) is removed (97) for compositional analysis (99). The pistons of a pressure intensifier (1) are driven to the top of their stroke using the pneumatic valve (27) and with the viscosity coil bypass valve (47) open. Hydraulic support fluid (9) and drive fluid (35) are driven oppositely to reverse the pistons in the pressure intensifiers (1). A flow rate jump occurs during the transition which indicates a liquid to gas phase transition. At the flow rate jump, the viscosity coil bypass valve (47) is open to a gas sampling device. At the next rate decrease, both pneumatic valves (27) are shifted to vent. Sample inlet valve (45) is shut. The volume of gas removed can be measured and the gas sampling device removed. A liquid sample device is then installed at sample inlet valve (45) and the valve (45) opened. The sample is collected by shifting both pneumatic valves (27) back to pressure, which drives the sample out. The addition of a compositional sampling valve (44) to the manifold allows a small fixed volume sample to be removed from the single phase sample stream (gas or oil) and directly delivered to analytical instruments such as a gas chromatograph, a high performance liquid chromatograph, laser spectrometer or mass spectrometry instrument.

If no material has been removed from the system (no compositional samples), the apparatus may be prepared for the next run and additional tests may be performed. The system temperature may be changed from oil field reservoir temperature to standard conditions. For example, 60° F. The sample (5) can be mixed until the new temperature has been stabilized. The system volume is then expanded until the pressure equals standard pressure. The gas and liquid volumes are then measured. Additionally, the formation volume factor measurement and gas oil ratio may be measured.

Separator tests may also be accomplished. The apparatus may be adjusted to the first stage separator temperature and target pressure. After mixing, the gas and liquid volumes are measured and a gas sample is removed from the apparatus for compositional analysis. The test can be repeated for the second stage separator temperature. Viscosity is also an important measurement at these stages.

Figure 6A:
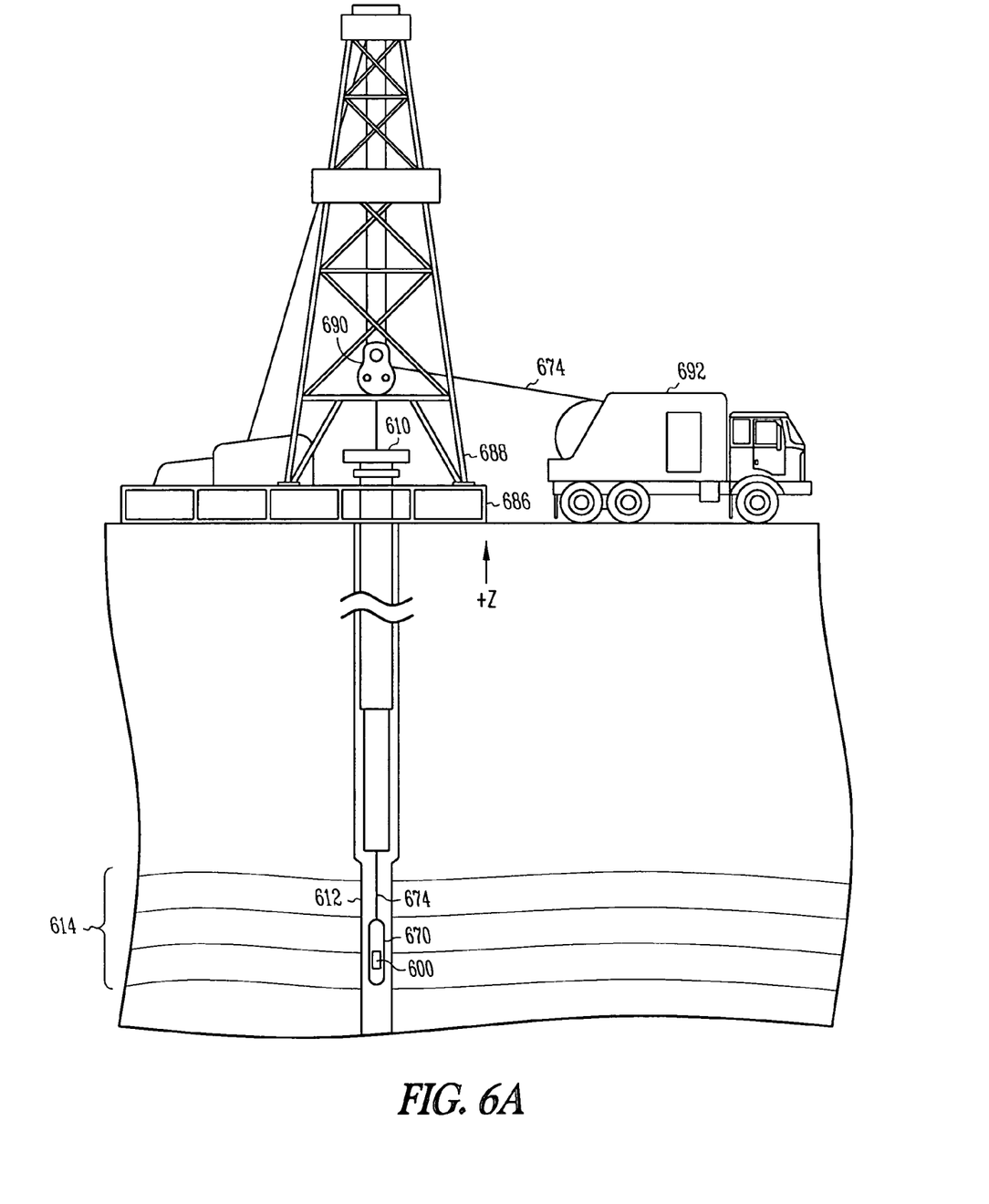
FIG. 6A illustrates a drilling well during wireline logging operations that may be used in acquiring of fluid samples, according to some embodiments of the invention.
Figure 6B:
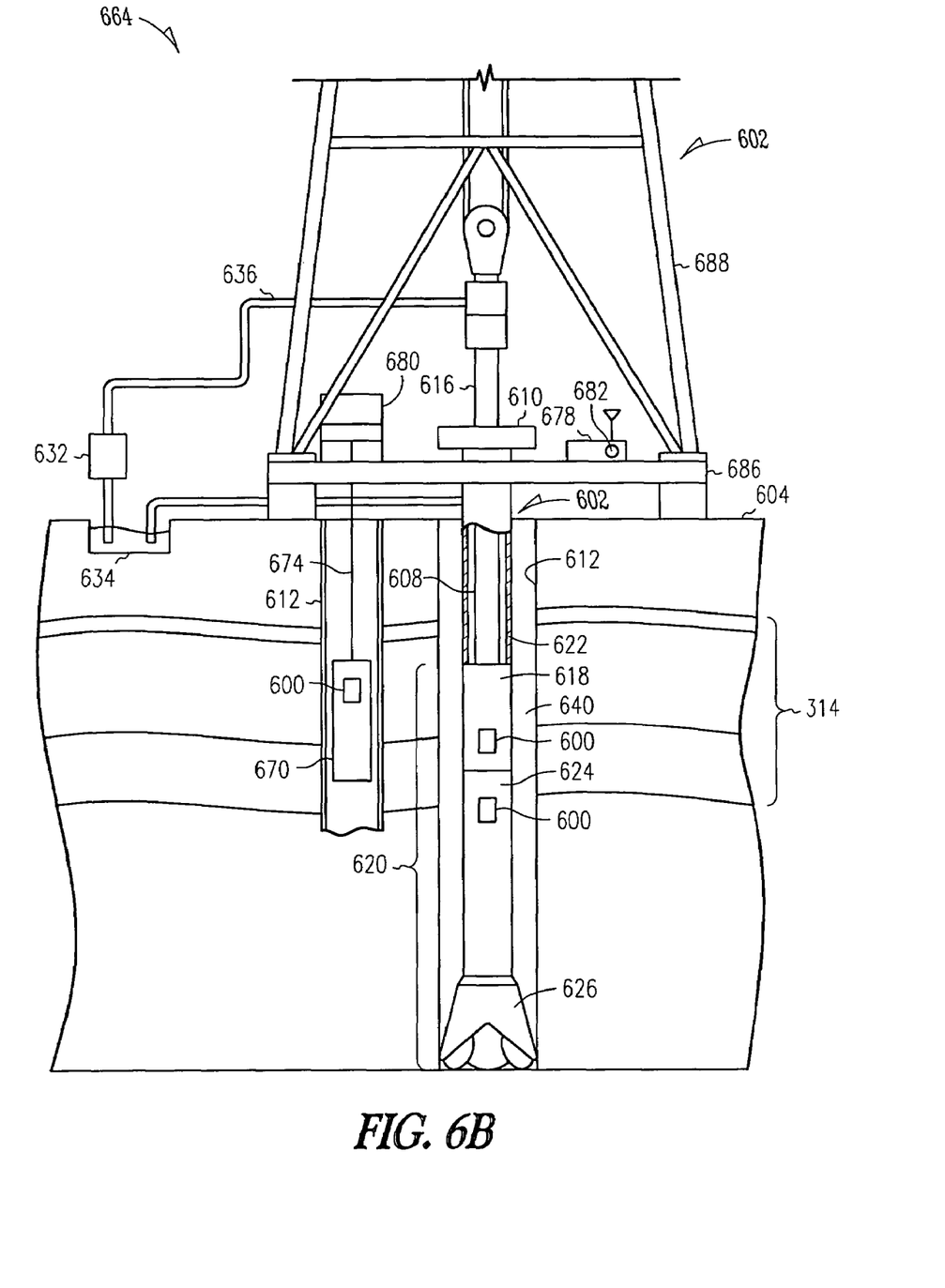
FIG. 6B illustrates a drilling well during MWD operations that may be used in acquiring of fluid samples, according to some embodiments of the invention.

System operating environments that may be used in conjunction with acquiring physical properties of fluid samples are now described. FIGS. 6A and 6B illustrate system operating environments for both wireline and Measurement While Drilling (MWD) operations, respectively.

FIG. 6A illustrates a drilling well during wireline logging operations that may be used in acquiring of fluid samples, according to some embodiments of the invention. A drilling platform 686 is equipped with a derrick 688 that supports a hoist 690. Drilling of oil and gas wells is commonly carried out by a string of drill pipes connected together so as to form a drilling string that is lowered through a rotary table 610 into a wellbore or borehole 612. Here it is assumed that the drilling string has been temporarily removed from the borehole 612 to allow a wireline logging tool body 670, such as a probe or sonde, to be lowered by wireline or logging cable 674 into the borehole 612. Typically, the tool body 670 is lowered to the bottom of the region of interest and subsequently pulled upward at a substantially constant speed. During the upward trip, instruments included in the tool body 670 may be used to perform measurements on the subsurface formations 614 adjacent the borehole 612 as they pass by. The measurement data can be communicated to a logging facility 692 for storage, processing, and analysis. The logging facility 692 may be provided with electronic equipment for various types of signal processing. Similar log data may be gathered and analyzed during drilling operations (e.g., during Logging While Drilling, or LWD operations).

FIG. 6B illustrates a drilling well during MWD operations that may be used in acquiring of fluid samples, according to some embodiments of the invention. It can be seen how a system 664 may also form a portion of a drilling rig 602 located at a surface 604 of a well 606. The drilling rig 602 may provide support for a drill string 608. The drill string 608 may operate to penetrate a rotary table 610 for drilling a borehole 612 through subsurface formations 614. The drill string 608 may include a Kelly 616, drill pipe 618, and a bottom hole assembly 620, perhaps located at the lower portion of the drill pipe 618.

The bottom hole assembly 620 may include drill collars 622, a downhole tool 624, and a drill bit 626. The drill bit 626 may operate to create a borehole 612 by penetrating the surface 604 and subsurface formations 614. The downhole tool 624 may comprise any of a number of different types of tools including MWD (measurement while drilling) tools, LWD (logging while drilling) tools, and others.

During drilling operations, the drill string 608 (perhaps including the Kelly 616, the drill pipe 618, and the bottom hole assembly 620) may be rotated by the rotary table 610. In addition to, or alternatively, the bottom hole assembly 620 may also be rotated by a motor (e.g., a mud motor) that is located downhole. The drill collars 622 may be used to add weight to the drill bit 626. The drill collars 622 also may stiffen the bottom hole assembly 620 to allow the bottom hole assembly 620 to transfer the added weight to the drill bit 626, and in turn, assist the drill bit 626 in penetrating the surface 604 and subsurface formations 614.

During drilling operations, a mud pump 632 may pump drilling fluid (sometimes known by those of skill in the art as "drilling mud") from a mud pit 634 through a hose 636 into the drill pipe 618 and down to the drill bit 626. The drilling fluid can flow out from the drill bit 626 and be returned to the surface 604 through an annular area 640 between the drill pipe 618 and the sides of the borehole 612. The drilling fluid may then be returned to the mud pit 634, where such fluid is filtered. In some embodiments, the drilling fluid can be used to cool the drill bit 626, as well as to provide lubrication for the drill bit 626 during drilling operations. Additionally, the drilling fluid may be used to remove subsurface formation 614 cuttings created by operating the drill bit 626.

In a cased hole where the formation is perforated and oil is flowing into the well bore, the bottom hole may be sampled with a variety of bottom hole sampling tools. Such tools may be run on a cable or tubing to near the producing formation and triggered (clocks, electric cable command, pressure). The sampler traps a representative sample of the fluid and is retrieved.

Advanced formation testers such as Reservoir Description Tool (RDT) (open hole wireline) and Geo Tap (measurement while drilling) are capable of placing a sealing probe on the wall of the well bore. The tools pump a volume of fluid out of the formation into a sample chamber within the tool. These sample chambers are retrieved when the tool is brought to surface. These chambers contain the sample upon which the embodiments of the present invention extract physical and chemical properties.

Figure 7:
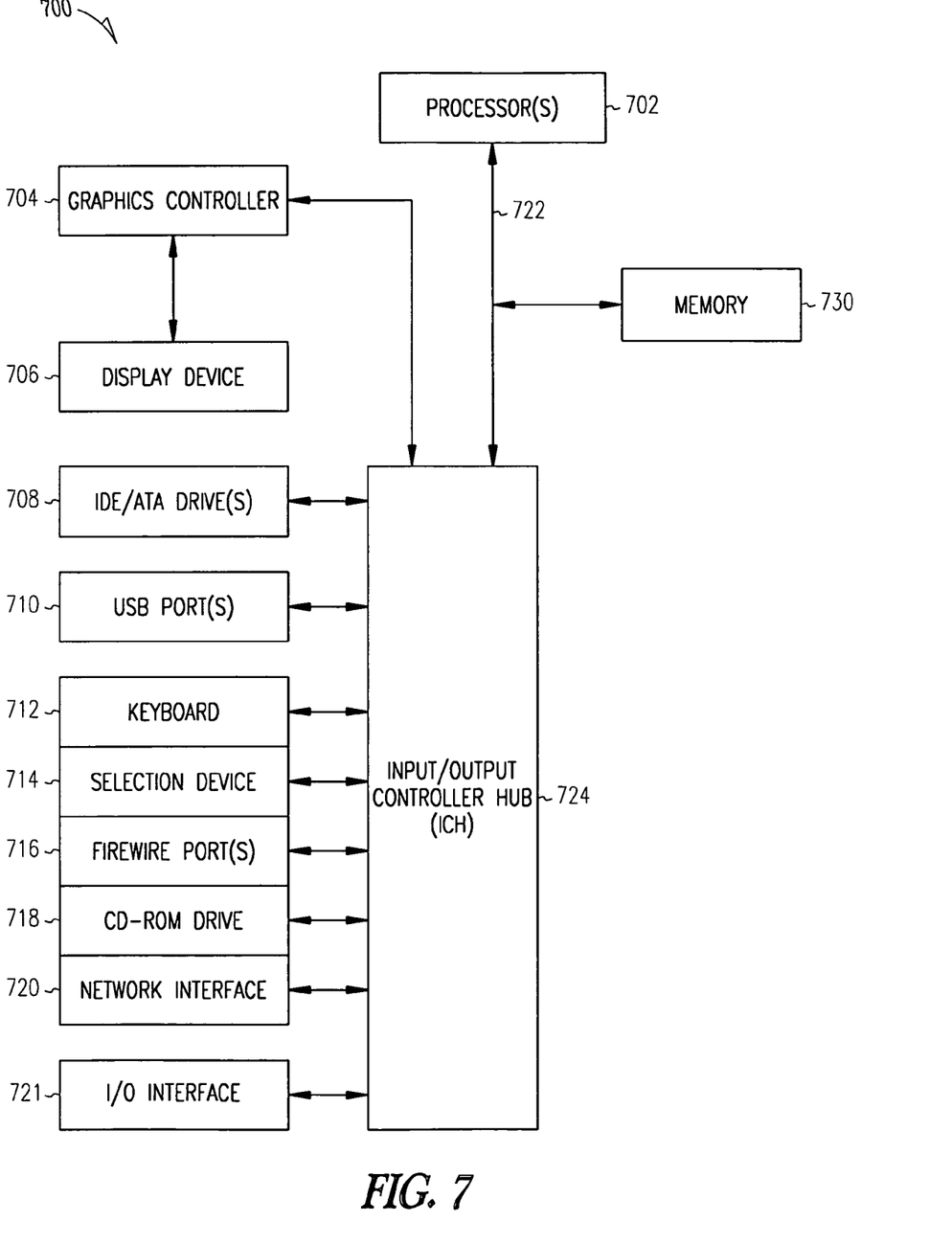
FIG. 7 illustrates a computer device that executes software that may be used to control some operations, according to some embodiments of the invention.

In some embodiments, at least part of the operations may be performed based on control by instructions executed by a computer. FIG. 7 illustrates a computer device that executes software that may be used to control some operations, according to some embodiments of the invention. The computer system 700 may be representative of a computer at the surface used to control the operations as described herein. The computer system 700 may be local or remote to the location of the apparatus described above.

As illustrated in FIG. 7, the computer system 700 comprises processor(s) 702. The computer system 700 also includes a memory unit 730, processor bus 722, and Input/Output controller hub (ICH) 724. The processor(s) 702, memory unit 730, and ICH 724 are coupled to the processor bus 722. The processor(s) 702 may comprise any suitable processor architecture. The computer system 700 may comprise one, two, three, or more processors, any of which may execute a set of instructions in accordance with embodiments of the invention.

The memory unit 730 may store data and/or instructions, and may comprise any suitable memory, such as a dynamic random access memory (DRAM). The computer system 700 also includes IDE drive(s) 708 and/or other suitable storage devices. A graphics controller 704 controls the display of information on a display device 706, according to some embodiments of the invention.

The input/output controller hub (ICH) 724 provides an interface to I/O devices or peripheral components for the computer system 700. The ICH 724 may comprise any suitable interface controller to provide for any suitable communication link to the processor(s) 702, memory unit 730 and/or to any suitable device or component in communication with the ICH 724. In some embodiments, the ICH 724 provides suitable arbitration and buffering for each interface.

For some embodiments of the invention, the ICH 724 provides an interface to one or more suitable integrated drive electronics (IDE) drives 708, such as a hard disk drive (HDD) or compact disc read only memory (CD ROM) drive, or to suitable universal serial bus (USB) devices through one or more USB ports 710. In some embodiments, the ICH 724 also provides an interface to a keyboard 712, a mouse 714, a CD-ROM drive 718, one or more suitable devices through one or more firewire ports 716. For one embodiment of the invention, the ICH 724 also provides a network interface 720 though which the computer system 700 can communicate with other computers and/or devices.

In some embodiments, the ICH 724 also provides a input/output (I/O) interface 721. The I/O interface 721 may be coupled to the apparatus described in FIGS. 1-5 above. Accordingly, the I/O interface 721 may accept input from such components of the apparatus as the piston position measurement device, pressure gauges, temperature controller, circulating pump, immersion heaters and spectrometer. The computer system 700 may process the input from such components, using for example software executing therein. Based on the processing, the computer system 700 may control, through the I/O interface 721, the operation of the electronic valves, pneumatic lines and the temperature control system which ultimately dictate the parameters under which the apparatus operates. Once the pneumatics lines, electronic valves and temperature control system have been manipulated, the I/O interface 721 may receive new input from the components previously mentioned. The computer system 700 may then determine the next set of parameters under which the apparatus is operated.

In some embodiments, the computer system 700 includes a machine-readable medium that stores a set of instructions (e.g., software) embodying any one, or all, of the methodologies for described herein. Furthermore, software may reside, completely or at least partially, within memory unit 730 and/or within the processor(s) 702.

It should also be understood that the apparatus and systems of various embodiments can be used in applications other than for drilling and logging operations, and thus, various embodiments are not to be so limited. The illustrations of apparatus and systems are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules, including multilayer, multi-chip modules. Such apparatus and systems may further be included as sub-components within a variety of electronic systems, such as televisions, personal computers, workstations, vehicles, and conducting cables for a variety of electrical devices, among others.

In the description, numerous specific details such as logic implementations, opcodes, means to specify operands, resource partitioning/sharing/duplication implementations, types and interrelationships of system components, and logic partitioning/integration choices are set forth in order to provide a more thorough understanding of the present invention. It will be appreciated, however, by one skilled in the art that embodiments of the invention may be practiced without such specific details. In other instances, control structures, gate level circuits and full software instruction sequences have not been shown in detail in order not to obscure the embodiments of the invention. Those of ordinary skill in the art, with the included descriptions will be able to implement appropriate functionality without undue experimentation.

In view of the wide variety of permutations to the embodiments described herein, this detailed description is intended to be illustrative only, and should not be taken as limiting the scope of the invention. What is claimed as the invention, therefore, is all such modifications as may come within the scope and spirit of the following claims and eqivalents thereto. Therefore, the specification and drawings are to be regarded in an illustrative rather than a restrictive sense.

What is claimed is:

1. An apparatus comprising:
    a sample manifold;
    a first pressure intensifier and a second pressure intensifier coupled to opposite ends of the sample manifold, wherein the first pressure intensifier and the second pressure intensifier are configured to move to push or pull a sample through the sample manifold to cause the sample to be approximately homogenous; and
    a viscosity coil coupled in a bypass relative to flow between the first pressure intensifier and the second pressure intensifier in the sample manifold, wherein the viscosity coil is configured to receive a part of the sample to measure a viscosity of the sample after a viscosity coil bypass valve is in a closed position, wherein the sample is to flow independent of the viscosity coil after the viscosity coil bypass valve is in an open position.

2. The apparatus of claim 1, wherein the first pressure intensifier and the second pressure intensifier each comprise a hydraulic support piston in contact with a hydraulic support fluid and a drive fluid, to push or pull the sample through the sample manifold.

3. The apparatus of claim 2, wherein the first pressure intensifier and the second pressure intensifier each comprise a sample piston coupled to the hydraulic support piston and in contact with the sample.

4. The apparatus of claim 1, wherein the viscosity coil is to measure the viscosity of the sample based on a known differential pressure and based on a measurement of flow rate through the viscosity coil.

5. The apparatus of claim 1, wherein a constant volume metering assembly receives a known volume of a hydraulic support fluid to expand the sample a known amount and based on a pressure change and based on the volume removed, a compressibility of the sample is measured.

6. The apparatus of claim 1, wherein a constant volume metering assembly receives a known volume of a hydraulic support fluid to expand the sample a known amount and based on a pressure change and based on the volume removed, a total sample volume of the sample is measured.

7. The apparatus of claim 1, wherein a constant volume metering assembly receives a known volume of a support fluid to expand the sample a known amount and based on a gas releasing and based on a pressure change, a bubble point of the sample is measured.

8. The apparatus of claim 1, wherein the sample manifold comprises a sample inlet valve to introduce or extract a sample.

9. The apparatus of claim 1, wherein the sample manifold comprises a viscosity bypass to flow the sample outside of the viscosity coil.

10. The apparatus of claim 1, wherein the sample manifold comprises sensors.

11. The apparatus of claim 10, wherein the sensors comprise density sensors, optical sensors, acoustic probes or a combination thereof.

12. The apparatus of claim 11, wherein the optical sensors comprise a spectrometer.

13. The apparatus of claim 12, wherein the spectrometer utilizes infixed energy, ultra violet energy or X-ray fluorescence.

14. The apparatus of claim 1, further comprising a drive mechanism to push or pull fluid through chambers of the first pressure intensifier and the second pressure intensifier.

15. The apparatus of claim 1, wherein a number of the one or more pressure intensifiers is two.

* * * * *

UNITED STATES PATENT AND TRADEMARK OFFICE
CERTIFICATE OF CORRECTION

PATENT NO. : 7,581,435 B2  Page 1 of 1
APPLICATION NO. : 11/240832
DATED : September 1, 2009
INVENTOR(S) : Michael T. Pelletier

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 718 days.

In Column 16, line 7, in Claim 13, delete "infixed energy," and insert -- infrared energy, --, therefor.

Signed and Sealed this

Fourteenth Day of September, 2010

David J. Kappos
*Director of the United States Patent and Trademark Office*